US012773252B2

(12) United States Patent
Marin et al.

(10) Patent No.: US 12,773,252 B2
(45) Date of Patent: Oct. 27, 2026

(54) COSMETIC COMPOSITION INTENDED FOR THE TREATMENT OF SKIN HYPERPIGMENTATION AND TREATMENT METHOD USING SAID COMPOSITION

(71) Applicant: CRYONOVE PHARMA, Chartres (FR)

(72) Inventors: Denis Marin, L'Etang la Ville (FR); Jean-Christophe Anton, Strasbourg (FR)

(73) Assignee: CRYONOVE PHARMA, Chartres (FR)

( * ) Notice: Subject to any disclaimer, the term of this patent is extended or adjusted under 35 U.S.C. 154(b) by 439 days.

(21) Appl. No.: 18/550,957

(22) PCT Filed: Mar. 15, 2022

(86) PCT No.: PCT/EP2022/056600
§ 371 (c)(1),
(2) Date: Sep. 16, 2023

(87) PCT Pub. No.: WO2022/194810
PCT Pub. Date: Sep. 22, 2022

(65) Prior Publication Data
US 2024/0148425 A1 May 9, 2024

(30) Foreign Application Priority Data
Mar. 18, 2021 (FR) ...................................... 2102728

(51) Int. Cl.
*A61B 18/02* (2006.01)
*A61B 18/00* (2006.01)
(Continued)

(52) U.S. Cl.
CPC ............ *A61B 18/0218* (2013.01); *A61K 8/69* (2013.01); *A61Q 19/02* (2013.01); *A61B 2018/0047* (2013.01); *A61K 2800/87* (2013.01)

(58) Field of Classification Search
CPC .......... A61K 2800/805; A61K 2800/87; A61K 8/69; A61K 31/19; A61K 31/60; A61K 45/06; A61K 47/12; A61K 8/315; A61K 8/368; A61K 9/0014; A61Q 19/02; B05B 12/12; A61P 17/12; A61B 18/02; A61B 2018/0293; A61B 2018/00041; A61B 2018/00452; A61B 2017/00747; A61B 18/0218; A61B 2018/0262; A61B 2017/00084; A61B 2018/00023; A61B 2018/00458; A61B 2018/00029; A61B 2018/0212; A61B 2018/00577; A61B 2017/00761; A61B 2018/00089; A61B 2018/00148; A61B 2018/00791; A61B 18/14; A61B 2017/00473; A61B 2018/00095; A61B 2018/0022; A61B 2018/0047; A61B 2018/00464; A61B 18/1492; A61B 18/203; A61B 2017/00792; A61B 2018/00017; A61B 2018/00434; A61B 2018/025; A61B 18/12; A61B 18/1477; A61B 18/18; A61B 2017/00017; A61B 2017/00292; A61B 2017/00539; A61B 2018/0016; A61B 2018/00476; A61B 2018/00583; A61B 2018/00642; A61B 2018/00702; A61B 2018/00875; A61B 2018/00982; A61B 2018/143; A61B 2018/1467; A61B 2090/378; A61B 90/361; A61B 18/1206; A61B 18/1402; A61B 18/148; A61B 18/1482; A61B 18/1485; A61B 18/149; A61B 2017/00026; A61B 2017/00097; A61B 2017/00101; A61B 2017/00247; A61B 2017/003; A61B 2017/22001; A61B 2017/22038; A61B 2018/00005; A61B 2018/00083; A61B 2018/0019; A61B 2018/00178; A61B 2018/00196; A61B 2018/00327; A61B 2018/00392; A61B 2018/00488; A61B 2018/00494; A61B 2018/00505;
(Continued)

(56) References Cited

U.S. PATENT DOCUMENTS

| | | | |
|---|---|---|---|
| 10,582,961 B2 | 3/2020 | Marin et al. | |
| 11,589,911 B2 | 2/2023 | Marin et al. | |

(Continued)

FOREIGN PATENT DOCUMENTS

| | | | |
|---|---|---|---|
| EP | 3045132 A1 | 7/2016 | |
| FR | 3045132 A1 * | 7/2016 | ............. A61B 18/02 |

(Continued)

OTHER PUBLICATIONS

JP2018505760A (Year: 2018).*
International Search Report and Written Opinion mailed Jul. 12, 2022, in connection with International Patent Application No. PCT/EP2022/056600, 11 pgs.
Mark D. Andrews, "Cryosurgery for Common Skin Conditions," 2004, American Family Physician, vol. 69, No. 10, pp. 2365-2372, XP05 5369 I I I.
Bunsho Kao et al., "Evaluation of Cryogen Spray Cooling Exposure on In Vitro Model Human Skin," 2004, Lasers in Surgery and Medicine, vol. 34, pp. 146-154.
(Continued)

*Primary Examiner* — Audrea B Coniglio
(74) *Attorney, Agent, or Firm* — Chiesa Shahinian & Giantomasi PC

(57) ABSTRACT

The present invention relates to a cosmetic composition intended for application to the epidermis for the treatment of skin hyperpigmentation, characterized in that it comprises from 1 to 7 doses of an atomized cryogenic fluid, the boiling point of which is between −196° C. and −19° C., each dose measuring between 0.048 mL and 0.56 mL, to a method for the in situ preparation of said composition, and to a cosmetic treatment method using said composition.

8 Claims, 3 Drawing Sheets

(51) Int. Cl.
*A61K 8/69* (2006.01)
*A61Q 19/02* (2006.01)

(58) Field of Classification Search
CPC .. A61B 2018/00601; A61B 2018/0066; A61B 2018/00678; A61B 2018/00726; A61B 2018/00744; A61B 2018/00761; A61B 2018/00797; A61B 2018/00821; A61B 2018/00827; A61B 2018/00886; A61B 2018/00994; A61B 2018/1213; A61B 2018/124; A61B 2018/1253; A61B 2018/126; A61B 2018/1273; A61B 2018/1407; A61B 2018/1425; A61B 2018/1472; A61B 2018/162; A61B 2018/165; A61B 2218/002; A61B 2218/007; A61B 17/22004; A61B 17/24; A61B 18/00; A61B 18/0206; A61B 18/06; A61B 18/08; A61B 18/082; A61B 18/1442; A61B 18/1815; A61B 18/20; A61B 2017/00106; A61B 2017/00172; A61B 2017/00269; A61B 2017/00353; A61B 2017/0046; A61B 2017/00477; A61B 2017/00774; A61B 2017/00946; A61B 2017/320069; A61B 2017/320089; A61B 2018/00011; A61B 2018/00065; A61B 2018/00113; A61B 2018/00291; A61B 2018/00351; A61B 2018/00357; A61B 2018/00404; A61B 2018/00613; A61B 2018/00738; A61B 2018/00773; A61B 2018/00779; A61B 2018/00785; A61B 2018/00863; A61B 2018/0281; A61B 2018/1823; A61B 2018/183; A61B 2018/2005; A61B 2018/20359; A61B 2090/036; A61B 2562/046; A61B 5/7405; A61B 8/08; A61B 8/0833; A61B 8/0858; A61B 8/13; A61B 8/14; A61B 8/4209; A61B 8/4236; A61B 8/4272; A61B 8/4281; A61B 8/4444; A61B 8/4461; A61B 8/4483; A61B 8/4494; A61B 8/461; A61B 8/469; A61B 90/30; A61B 90/37; A61B 90/50
See application file for complete search history.

(56) References Cited

U.S. PATENT DOCUMENTS

| | | | |
|---|---|---|---|
| 2010/0087806 A1 | 4/2010 | Da Silva et al. | |
| 2017/0354451 A1 | 12/2017 | Marin et al. | |
| 2021/0059738 A1 | 3/2021 | Marin et al. | |

FOREIGN PATENT DOCUMENTS

| | | | | |
|---|---|---|---|---|
| FR | 3076200 A1 | | 7/2019 | |
| JP | 2018505760 A | * | 3/2018 | ......... A61B 18/0218 |
| WO | 2016113305 A1 | | 7/2016 | |
| WO | 2019129827 A1 | | 7/2019 | |

OTHER PUBLICATIONS

Gage AA et al., “Effect of varying freezing and thawing rates in experimental cryosurgery,” 1985, Cryobiology, vol. 22, No. 2, pp. 175-182.

Har-Shai Y et al., “Effect of skin surface temperature on skin pigmentation during contact and intralesional cryosurgery of keloids,” 2006, Journal of European Academy of Dermatology & Venereology, vol. 21, Issue 2, pp. 191-198.

Raidan M. et al., “Effect of Cooling to Low Temperatures on Viability of Human Skin Keratinocytes at Different of Differentiation,” 2010, Cell and Tissue Biology, vol. 4, No. 6, pp. 529-538.

Burge SM et al., “Pigment changes in human skin after cryotherapy,” 1986, Cryobiology, vol. 23, Issue 5, pp. 422-432.

Enas A. S. Attia, M.D. et al., “Cryotherapy versus phenol chemical peeling for Solar lentigines: a clinical, histologic, immunohistochemical and ultrastructural study,” 2010, J Egypt women. Dermatol SOC, pp. 87-96.

Croning, “General Guide for Cryogenically Storing Animal Cell Cultures,” retrieved online on Sep. 14, 2023, from: https://www.corning.com/worldwide/en/products/life-sciences/resources/webforms/we-get-you-guide-for-cryogenically-storing-animal-cell-cultures.html, 14 pgs.

* cited by examiner

[Fig. 1]
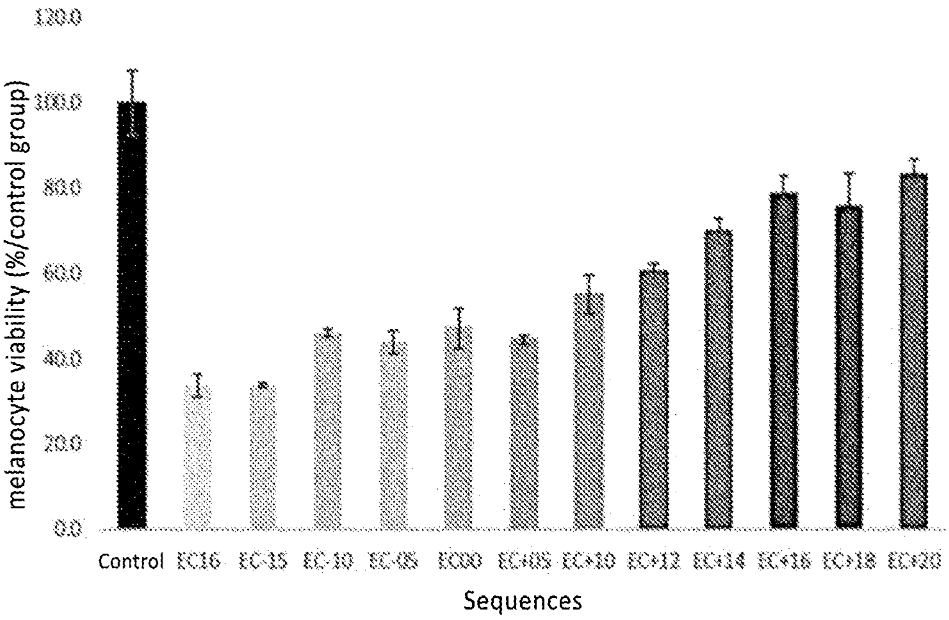
[Fig. 2]
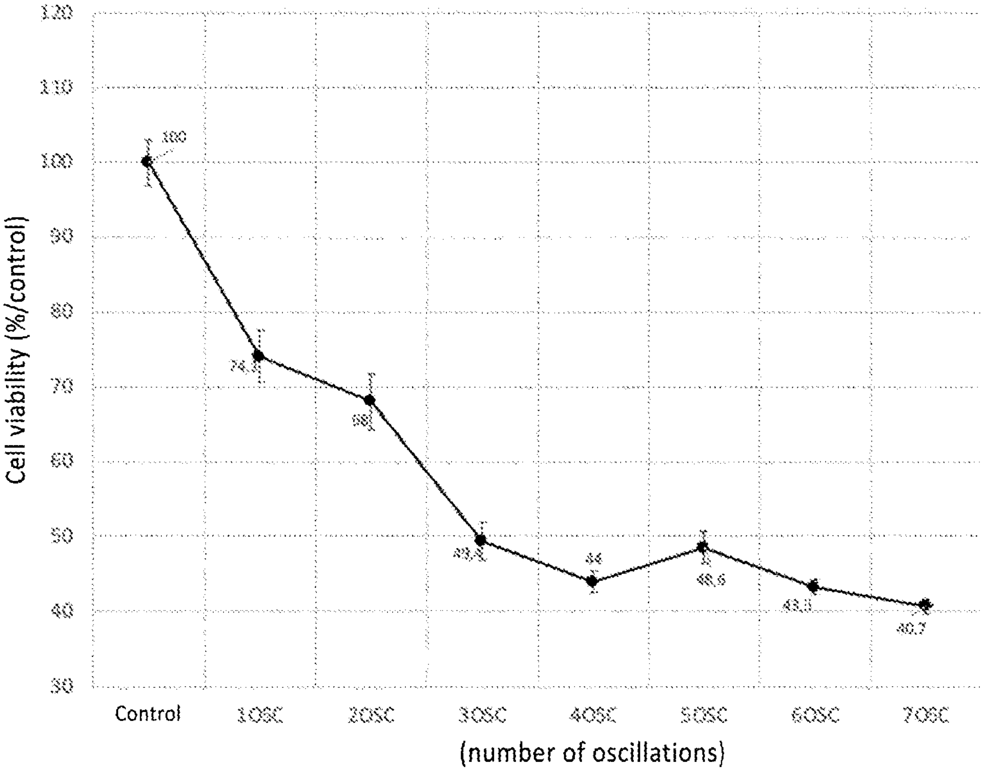

[Fig. 3]
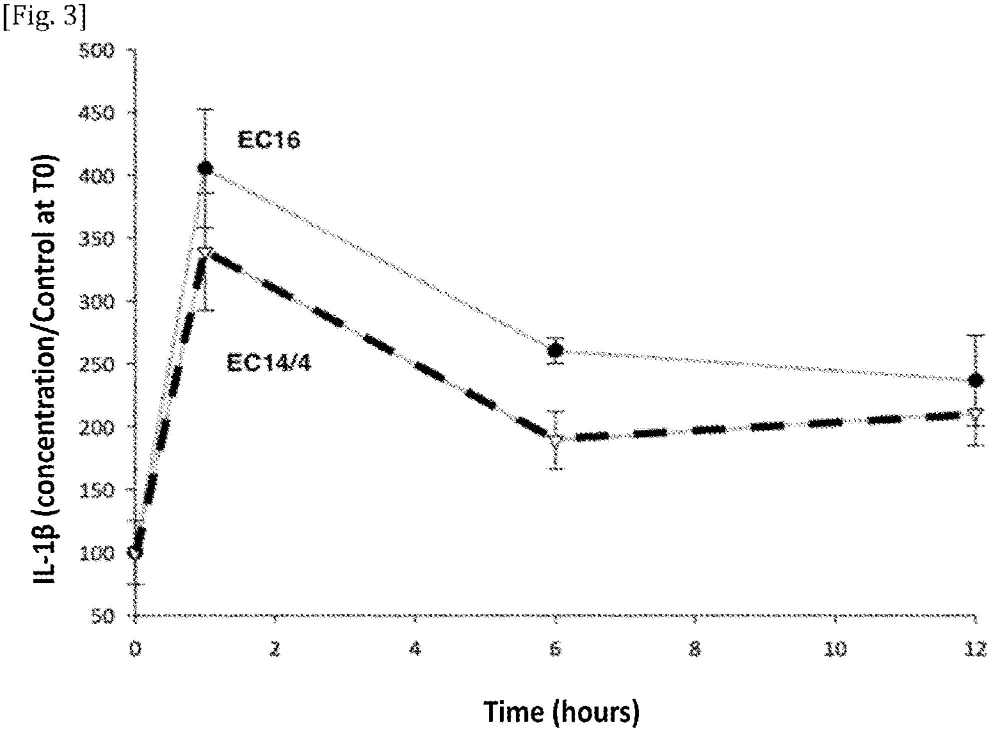
[Fig. 4]
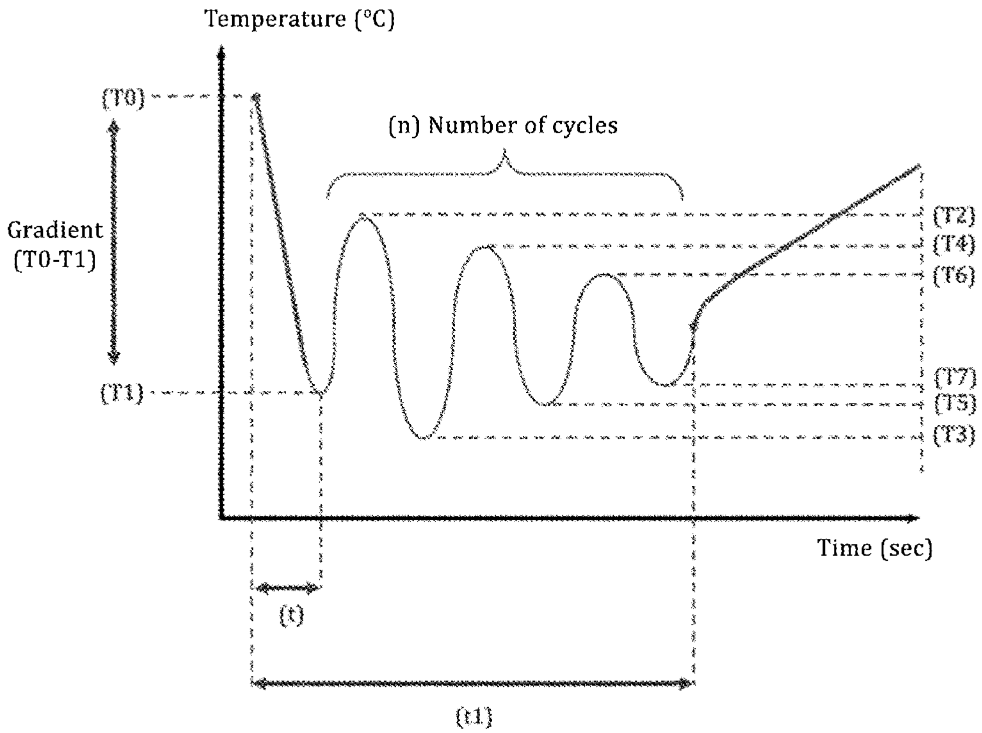

[Fig. 5]
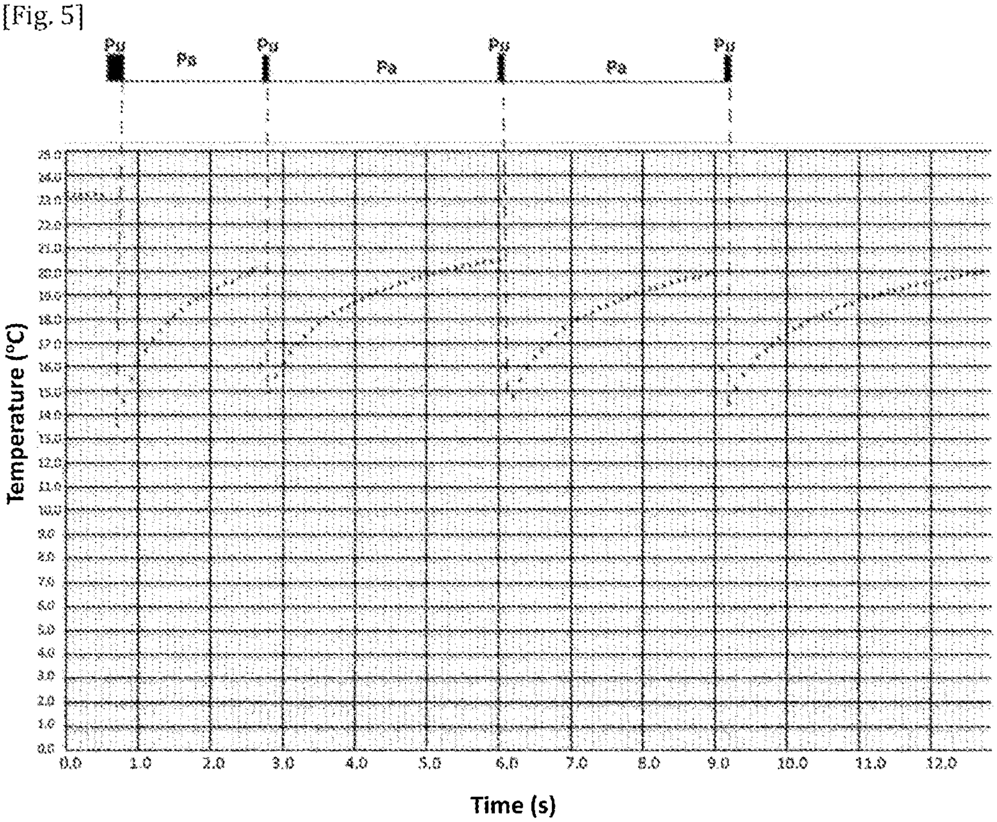

COSMETIC COMPOSITION INTENDED FOR THE TREATMENT OF SKIN HYPERPIGMENTATION AND TREATMENT METHOD USING SAID COMPOSITION

CROSS-REFERENCE TO RELATED APPLICATION(S)

This application is a National Stage under 35 U.S.C. 371 of International Patent Application No. PCT/EP2022/056600, filed Mar. 15, 2022, which claims the benefit of priority under 35 U.S.C. 119 to French Patent Application No. 2102728, filed Mar. 18, 2021; the disclosures of all of which are incorporated herein by reference in their entirety.

The invention applies to the field of cosmetics and relates more particularly to a cosmetic composition comprising a cryogenic fluid as well as to a method for treating skin hyperpigmentation cryogenically using said composition.

Cryogenics is generally used in cosmetics to eliminate dark spots. Dark spots, also called age spots, are small skin spots of variable size which appear on the skin areas exposed to the sun such as the face, the hands, the shoulders or the arms. Dark spots are considered to be benign cosmetic deformities and are often unsightly. They are generally treated by cosmetic methods comprising the application of creams to the skin or by cryogenics.

Traditional cryogenic treatment methods are implemented, for example, by means of an atomizing device locally spraying a cryogenic fluid (liquid nitrogen, di-methyl-ether, di-fluoroethane, tetrafluoroethane, etc.) onto the epidermis at subzero temperatures in one or more freeze/thaw cycles.

By reaching very precise subzero temperatures in sequences of very short durations, it is possible to exert a so-called cyto-selective action so as to eliminate only the cells (melanocytes) responsible for skin hyperpigmentations such as dark spots, without producing any deleterious effect on the other cells. This method of cyto-selective action makes it possible to preserve, in particular, keratinocytes, because such cells are less sensitive to cold than the melanocytes.

More specifically, the cyto-selective treatment of hyperpigmentations is obtained by a cryogenic sequence consisting of a succession of cycles comprising very rapid freezing followed by a slow warming during which the destructive action of the melanocytes will be prolonged.

Indeed, generally, the very sudden lowering of the temperature of the epidermis to a subzero temperature causes, even before the cellular tissue is solidified, a micro-crystallization of the intracellular water which induces, both membrane alterations and denaturation of the structural proteins and enzymatic systems, such conditions leading to a deleterious effect on the cell (cell lysis by mechanical shock).

During these cycles, another phenomenon takes place, called osmotic shock. Very sudden lowering of the temperature followed by slow warming, in the form of several consecutive cycles, will cause crystallization of the extracellular water, followed by changes to the concentrations of extra- and intracellular elements (including ions) causing concentration gradients. The intracellular liquid will therefore move toward the extracellular medium during the cooling phase (or just after), then again rejoin the intracellular compartment during the heating phase, and this occurs several times in a row based on the cycles. Ultimately, the cell will no longer be able to manage these liquid movements and the osmotic shock will cause cell lysis.

More precisely, it is found that during the very rapid cooling phase, ice microcrystals form in the extracellular medium. The consequence is the formation of a concentration gradient between the extracellular and intracellular media, and therefore a movement of water from the intracellular medium to the extracellular medium. The cell's volume is then reduced. After cooling the temperature of the epidermis, its rise in temperature up to +34° C. lasts and is therefore a slow phenomenon (typically from 10 to 100° C./min), unlike the decrease in temperature. During this phase, the extracellular microcrystals melt, and this time, a new phenomenon occurs in the form of reversing the gradient between the extracellular medium and the intracellular compartment. Indeed, the water which is in large quantities in the extracellular medium, massively enters the cells to compensate for this gradient and causes an intracellular edema resulting in a swelling of the cell and a rupture of its membrane. A phenomenon of cell lysis is then again carried out, not by the formation of microcrystals but by a cell dehydration/rehydration mechanism. This is what is called osmotic shock.

There are cryogenic devices such as that described in patent application WO 2016/113305 intended for the implementation of a cyto-selective treatment of dark spots. This device ensures the controlled atomization (to within a hundredth of a second) of a cryogenic fluid intended to lower and maintain, for a few seconds, the temperature of the epidermis between −5° C. and −20° C. then to perform a slow rise in temperature to obtain lysis, that is to say destruction, melanocytes and, accordingly, elimination of dark spots.

To this end, the device comprises a pressurized cryogenic gas cartridge having specific physical properties, a spray nozzle ensuring the delivery of a precise dose of cryogenic gas from the cartridge by being coupled to automated timing means and a nozzle intended to concentrate, diffuse and apply the gas flow in a precise and homogeneous manner over a determined skin area. Such a nozzle is described, in particular, in FR3076200A1.

The effect of cold on the epidermis has already been widely studied and analyzed, in particular, by the article [Bunsho Kao et al. *Evaluation of Cryogen Spray Cooling Exposure on In Vitro Model Human Skin. Lasers in Surgery and Medicine* 34:146-154 (2004)] that has shown that mechanical shock produced by very rapid freezing causes the formation of ice microcrystals inside and outside the melanocyte cells, resulting in the breaking of the cell wall and the death of the cell.

The osmotic shock, by differences in osmotic pressure gradient between the intra and extracellular media, will also cause the lysis of the melanocytes. Subsequently, within a period of 2 to 4 weeks which corresponds to the average cell renewal time, the organism gradually removes the cell elements and the melanin until the hyperpigmentation has completely disappeared.

Other scientific studies, including that of GAGE et al. [Gage A A et al. *Effect of varying freezing and thawing rates in experimental cryosurgery. Cryobiology.* 1985 April; 22(2):175-82], have the results of cryotherapy tests carried out on the epidermis in different subzero temperature ranges. The protocol usually used for these tests comprises a rapid freezing phase and a slow thawing phase. The cell damage observed is due to the formation of ice crystals and is associated with a failure of blood microcirculation after the thawing phase. Indeed, the rupture of the blood circulation deprives the epidermis cells of a chance of survival, which leads to a preference for a short cooling phase.

Histological sections have shown the viability of melanocytes for 7 days after applying a temperature between 0 and −4° C. For temperatures below −4° C., cell damage appears in the melanocytes and no pigments are observed one week after the application of the cold.

From −4° C. to −7° C., certain types of cells are still living at the deep layers of the epidermis, but there are no longer any melanocytes. The disaggregation of the melanocytes occurs for several days, the melanin is fragmented and then the melanocytes disappear from the deep layers. In fact, the melanosomes containing melanin are phagocytosed by neighboring keratinocytes, the enzymes of which digest the membrane, as shown by the observation of electron microscopy biopsies.

From −7° C. to −30° C., no more melanocytes are observed, nor melanin. However, re-pigmentation toward the physiological (natural) pigmentation of the skin occurs 4 months after applying cold in a temperature range between −4° C. and −30° C. In fact, the re-pigmentation of the treated zone is carried out from the melanocytes present at the periphery of the treated zone.

If the temperature applied to the epidermis falls to −40° C., the total disappearance of the melanocytes and melanin is observed. Permanent depigmentation of the skin is then witnessed.

Studies [Har-Shai Y et al. *Effect of skin surface temperature on skin pigmentation during contact and intralesional cryosurgery of keloids. JEADV* 2007, 21, 191-198] further specify that the melanocytes remain viable only if they are subjected to a temperature above −4° C. Indeed, between −4° C. and −7° C., lysis of the granules containing the pigments (melanosomes containing melanin) is observed and, subsequently, a start of enzymatic digestion of the melanin in the melanocytes and in keratinocytes (in the deep layer of the epidermis, therefore close to the basal layer).

RAIDAN et al. [Raidan M et al. *Effect of Cooling to Low Temperatures on Viability of Human Skin Keratinocytes at Different Stages of Differentiation. Cell and Tissue Biology,* 2010, Vol. 4, No. 6, pp. 1-10] conducted cell viability studies of keratinocytes treated by cold in a temperature range of −10° C. to −70° C. The preservation of keratinocytes is essential since these cells have the ability to reform all the layers of the epidermis.

It emerges from these studies that the destruction of keratinocytes occurs for temperatures below −35° C., with a very significant elimination of the melanocytes. Thus, the action of a temperature between −5° C. and −20° C. would make it possible to act on melanin and the melanocytes, without damaging the keratinocytes, according to the principle of cyto-selectivity.

BURGE et al. [Burge S M et al. *Pigment changes in human skin after cryotherapy. Cryobiology,* 1986, 23:422-432] have shown that after a brief 5-second cooling of the skin by atomizing liquid nitrogen at −196° C. over a margin of 1 to 5 mm beyond the wound to be treated, hypopigmentation persists and that extending the application of the cold by 15 seconds would cause the melanosomes in the keratinocytes to completely disappear.

In ANDREWS [Andrews M K et al. *Cryosurgery for common skin conditions. Am fam physician,* 2004, 69 (10): 2365-2373], a liquid nitrogen spray makes it possible to reach a temperature of −50° C. at an epidermis depth between 4 mm and 5 mm. These authors therefore hypothesize that the hypopigmentation may be due to a decrease in the number of melanocytes, to a decrease in the production of the number of melanosomes, or to a blocking of the transfer of melanosomes to the keratinocytes, and conclude that the cryotherapy alters epidermal control.

Moreover, GAGE A A et al. (1985) have shown that a temperature below −50° C. leads to necrosis of the tissues and, on the other hand, for freezing temperatures greater than −15° C., the tissue remains viable regardless of the thaw program used. However, they also observed that slow thawing of the tissue between 5 and 7 minutes is also harmful since large ice crystals are formed which cause intracellular dehydration.

Therefore, a method comprising rapid freezing (between 30 seconds and 2 minutes) to temperatures between −15° C. and −50° C. with maintaining that temperature (for 3 minutes) followed by slow thawing (between 5 and 7 minutes), represents the most aggressive experimental scheme for the epidermis.

Conversely, rapid thawing (less than 2 minutes) leads to less necrosis regardless of the program used with a total absence of necrosis if it follows slow freezing (3 minutes) between −15° C. and −24° C.

Moreover, a clinical study was carried out by ATTIA et al. [Attia E A S et al. *Cryotherapy versus phenol chemical peeling for Solar lentigines: a clinical, histologic, immunohistochemical and ultrastructural study. J Egypt women. Dermatol SOC,* 2010, 7:87-96, 2010] on twenty patients with actinic lentigines on the back of their hands which were treated with liquid nitrogen. A cooling cycle of 3 to 5 seconds was carried out until the wound froze. Biopsies carried out 3 weeks after the treatment show that cryotherapy reduces skin pigmentation. This result is due to a reduction in the number of melanocytes and also to a reduction in the size and aggregates of the granules of melanin in the melanocytes and the keratinocytes, corroborated by the histological sections and electron microscopy.

In light of these previous studies, the results of which are set out above, the person skilled in the art could therefore deduce therefrom that the optimal efficacy of a cryogenic method intended for treating skin hyperpigmentation, and therefore aiming at the elimination of the melanocytes while preserving keratinocytes, is within a temperature range of the epidermis between −5° and −20° C.

However, all these studies also show that, when the epidermis is brought to subzero temperatures, epidermal control is altered and, concomitantly, inflammatory processes or severe irritations occur.

Furthermore, the application to the epidermis of a cryogenic fluid at a very low temperature also has the risk of destroying cells other than the melanocytes as well. This risk is particularly critical with respect to keratinocytes which play an essential role in the regulation of melanogenesis. All these side effects are problematic in the context of a cosmetic treatment of skin hyperpigmentation because they generate major side effects: pain during application and post-treatment of hyperpigmentation, inflammation, scabbing, edema, blisters, hypo-pigmentation, scarring, etc.).

However, experiments carried out in the context of the development of the invention have revealed that, contrary to a dose-dependent effect (dependent on the amount of cryogenic fluid applied) for which it could be expected, the mortality curve of the melanocytes as a function of the temperature reached (called the target temperature or arrival temperature) is formed of several parts which are not all dose-dependent and one of which in particular is stable over a temperature range of 0° C. to +10° C. (see FIG. 1).

By way of example, when the viability of the melanocytes is compared between the application of a dose of atomized cryogenic gas making it possible to reach a target temperature of −10° C. (sequence referenced EC-10) on the epidermis from its normal starting temperature (34° C.) in an environment at room temperature (23° C.), and the application of a dose making it possible to reach a temperature of 0° C. (sequence referenced EC00), it is observed that this viability remains the same whereas it could have been expected to be quite different (the dose of cryogenic gas of the sequence EC00 being lower).

In addition, these experiments have shown that it was possible to reduce the viability of the melanocytes with above-zero target temperatures of the epidermis (see FIG. 1). By way of example, when a dose of gas is applied to the melanocytes making it possible to achieve a temperature of +12° C. on the epidermis, the viability of the melanocytes decreases by 40% relative to the control group (untreated melanocytes serving as a control group).

Furthermore, tests at above-zero target temperatures also revealed that several consecutive temperature oscillations made it possible to increase the reduction in the viability of the melanocytes relative to a single variation (see FIG. 2). FIG. 2 shows the viability of the melanocytes as a function of the number of temperature oscillations produced on the cells. For a target temperature of +14° C., the melanocytes subjected to 1 oscillation (1 osc) have a viability which decreases to 74.1% whereas melanocytes subjected to 4 consecutive oscillations see their viability decrease to 44%. Thus, such oscillations could be applied by virtue of a sequence of successive atomizations of a selected cryogenic gas intended to generate, at the surface of the epidermis, oscillations of its temperature.

Finally, on the other constituent cells of the epidermis (keratinocytes), experiments have shown that oscillations within an above-zero temperature range caused a lesser effect on certain irritation markers compared to the application of a single cryogenic gas within a subzero temperature range while causing an identical reduction in the viability of the keratinocytes (see FIG. 3). Thus, if the marker (IL-1β) is considered, the irritant effect resulting from the application of doses of cryogenic gas making it possible to achieve a target epidermis temperature of +14° C. with a series of 4 successive oscillations is less than that observed with a dose making it possible to achieve subzero temperatures, and this is true for the same level of keratinocyte viability. Likewise, since the irritation is directly related to the mortality induced by keratinocytes, it could have been thought that for an identical reduction in viability, the irritation would be identical.

Thus, it turns out that a target epidermis temperature in an above-zero temperature range associated with a determined number of successive atomizations of cryogenic gases (producing temperature oscillations at the epidermis) jointly have an influence on the mortality rate of the cells at the origin of hyperpigmentation.

Indeed, the results of the experiments conducted in the context of the development of the invention show that, contrary to the conclusions of the preceding studies, the viability of these cells is significantly reduced with target temperatures well above zero (+14° C. for example for a series of 1 to 4 oscillations). However, the formation of ice crystals, which constitutes the main cause known for mechanical shocks causing the rupture of the membranes and cell lysis, cannot obviously occur with above-zero temperatures. Likewise, osmotic shocks too are not supposed to appear unless, there is formation of ice crystals in the extracellular medium, which is obviously impossible with above-zero temperatures.

In this context, the invention makes it possible to both solve the technical problems posed by the prior methods and overcome a technical preconception. Indeed, the invention shows that it is possible, contrary to the recommendations of the prior art under consideration, to obtain a large decrease in the viability of the melanocytes and also a lower irritation produced by the keratinocytes (and therefore an effective elimination of skin hyperpigmentation) by using a cryogenic and cyto-selective cosmetic treatment characterized by a series of oscillations in the temperature of the epidermis, for very short periods, while keeping the epidermis in an above-zero temperature range.

This aim is achieved, according to the invention, by means of a cosmetic composition intended for application to the epidermis for the treatment of skin hyperpigmentation, characterized in that it comprises from 1 to 7 doses of an atomized cryogenic fluid whose boiling point is between −196° C. and −19° C., each dose measuring between 0.048 mL and 0.56 mL.

The invention has selected four specific formulations of this cosmetic composition, the effects of which are more particularly advantageous.

Thus, according to a first formulation, the composition of the invention comprises a single dose of 0.08 mL of atomized 1,1-difluoroethane.

According to a second formulation, the composition comprises 4 doses of atomized 1,1-difluoroethane, each dose being between 0.048 mL and 0.144 mL.

According to a third formulation, the composition comprises 2 doses of atomized 1,1-difluoroethane, respectively, of 0.064 mL and 0.176 mL.

According to a fourth formulation, the composition comprises 7 doses of atomized 1,1-difluoroethane, each dose being between 0.40 mL and 0.56 mL.

Another object of the invention is a method for preparing a cosmetic composition intended for application to the epidermis for the treatment of skin hyperpigmentation, characterized in that it comprises the in situ formulation of 1 to 7 doses of a cryogenic gas, the boiling point of which is between −196° C. and −19° C., by a sequence (EC) of successive atomizations of said gas at a flow rate of between 0.1 mL/s and 2.0 mL/s, the respective durations of which are between 0.01 second and 1 second.

A further object of the invention is a method for cosmetic treatment of skin hyperpigmentation by means of a pressurized cryogenic fluid cartridge and a device comprising a solenoid valve controlled by an electronic timing system and ensuring the expansion of the fluid from said cartridge and a spray nozzle ensuring its ejection and atomization onto the epidermis, characterized in that a sequence of successive atomizations of said fluid is carried out on the epidermis to create, within an above-zero temperature range, a series of oscillations of its temperature, the total duration of which is between 2.1 seconds and 250 seconds, each consisting of an abrupt cooling phase at a temperature descent rate comprised between 50° C./s and 170° C./s followed by a slower warming phase.

Therefore, according to the treatment method of the invention, a cosmetic composition is prepared comprising a first dose of atomized cryogenic gas that is applied for a very short duration on the epidermis to lower its temperature to a target temperature (for example, from +14° C., the epidermis being initially at 34° C.). Then, its temperature is left to rise to its initial value (or to a lower value but still less than or equal to 20° C.) and this operation is optionally repeated several times (up to 7 times) by applying a new dose of atomized fluid to the epidermis. However, not all doses successively applied to the epidermis are necessarily identical.

In all cases, the doses are determined such that the temperature of the epidermis does not drop below 0° C. Each of these operations thus corresponds to an oscillation of the temperature of the epidermis. The invention has shown that the viability of the melanocytes is dependent on the oscillations and the number of oscillations, up to 4 consecutive oscillations.

According to an advantageous feature of the method, the duration of each atomization is between 0.01 seconds and 1 second.

According to another feature, the duration of each of the oscillations is between 2.1 seconds and 3 seconds.

Preferably, the phase of warming the oscillations corresponds to a rise in temperature of between 20° C. and 34° C.

According to a preferred embodiment of the treatment method of the invention, the number of successive oscillations of the temperature of the epidermis in a series is between 1 and 7.

According to the invention, it is provided that the temperature of the epidermis is cooled to a target temperature of between 0° C. and 14° C.

Furthermore, the phase of cooling the epidermis is carried out according to a gradient of at least 15° C. from an initial temperature of between 29° C. and 37° C. (as this range of temperatures covers the differences in temperature of the epidermis from one individual to another and as a function of the external environment).

According to yet another feature, the cryogenic fluid is a gas whose boiling point is between −196° C. and −19° C.

Preferably, cryogenic gas is selected from the group consisting of 1,1-difluoroethane, the boiling point of which is −24.7° C. (under normal pressure of 1 atmosphere i.e. 1.013 bar), methoxymethane, 1,1,1,2-tetrafluoroethane, trans-1,3,3,3-tetrafluoropropene, butane/propane mixtures respectively having boiling temperatures (under normal pressure of 1 atmosphere, i.e. 1.013 bar), −196° C., −24° C., −26.3° C. and −19° C. (depending on the proportions of said mixture).

According to a specific variant of the cosmetic treatment process, said sequence is implemented by means of a single atomization of 1,1-difluoroethane at 0.8 mL/second for a duration of 0.1 second so as to achieve a target epidermis temperature of 14° C.

Thus, for a sequence making it possible to carry out a single oscillation from 34° C. to a temperature of +14° C., the total duration of the oscillation, comprising the descent in temperature of the epidermis and then its rise to a temperature of +20° C. is 2.1 seconds.

According to a first variant of the method, said sequence is implemented by means of 4 successive atomizations of 1,1-difluoroethane at 0.8 mL/second, each having a duration comprised between 0.06 seconds and 0.18 seconds so as to achieve a target epidermis temperature of 14° C. after each atomization.

According to a second variant of the method, said sequence is implemented by means of 2 successive atomizations of 1,1-difluoroethane at 0.8 mL/second, each having a duration comprised between 0.22 seconds and 0.08 seconds so as to achieve a target epidermis temperature of 12° C. after each atomization.

According to a third variant of the method, said sequence is implemented by means of 7 successive atomizations of 1,1-difluoroethane at 0.8 mL/second, each having a duration comprised between 0.5 seconds and 0.7 seconds so as to achieve a target epidermis temperature of 0° C. after each atomization.

This third variant of the method is implemented during a cumulative duration of the atomizations of 3.9 seconds so as to achieve a target epidermis temperature of 0° C. after each atomization followed by raising the temperature to at least 20° C.

Therefore, doses of the cryogenic fluid entering the cosmetic composition of the invention are successively atomized and applied to the skin and, more precisely on the epidermis, at regular, very close intervals. Such a sequence of atomizations leads to sudden phases of cooling the skin followed by pauses leading to slower warming phases. These successive phases thus result in a series of oscillations of the temperature of the epidermis which correspond to a sequence of atomizations of the cosmetic composition, within the meaning of the present invention. This atomization sequence consists of micro-atomizations (or pulses), forming that many doses of cryogenic gas, interspersed with pauses. For example, the atomization sequence EC14/4 osc. comprises 4 atomizations followed by pauses whose respective durations are indicated in Table 2 below.

A sequence is therefore characterized by a given number of cryogenic fluid atomizations and a corresponding number of oscillations of the epidermis temperature. These oscillations are independent of each other and each oscillation is itself defined, on the one hand, by a temperature gradient between a starting temperature (the epidermis generally being at 34° C.) and a lower but still above-zero temperature (called target temperature) of the epidermis and, on the other hand, a temperature descent mechanism whose speed is specifically between 50° C./s and 170° C./s resulting from the application of the cryogenic fluid.

Other features and advantages of the invention will emerge on reading the following disclosure, with reference to the appended figures and detailed hereinafter.

FIG. 1 is a graph showing various embodiments of the invention with the variations in the mortality rate of the melanocytes as a function of the temperatures applied according to different sequences.

FIG. 2 is a graph showing various embodiments of the invention with variations in the viability of the melanocytes as a function of an applied target temperature (+14° C.) according to several oscillations.

FIG. 3 is a graph showing the variation over time of the (IL-1β) marker of the irritation for keratinocytes subjected to two sequences making it possible to achieve the same level of viability, a sequence (EC16) located in a subzero temperature range (−16° C.) and the other sequence (EC14) in an above-zero temperature range (+14° C.).

FIG. 4 is a graph representing a preferential sequence of the cosmetic treatment method of the invention with the variations in temperature as a function of time in the form of a series of oscillations.

FIG. 5 are graphs representing, respectively, the variations in the temperature of the epidermis as a function of time (curves in the lower part) in relation to a preferential sequence of atomizations (top diagram) for the implementation of the treatment method of the invention.

For greater clarity, identical or similar elements are identified by identical reference signs in the description and in the figures.

Naturally, the embodiments of the composition of the invention and the various implementations of the cosmetic treatment method of the invention shown by the figures presented above and described below are given only by way of non-limiting examples. It is explicitly provided that it is possible to propose and combine various modes to propose others.

The invention relates to the field of cosmetic and cryogenic treatment of skin hyperpigmentation and, in particular, to the elimination of so-called dark spots that appear on the epidermis.

In general, the analysis of the scientific literature reveals that cell destruction or "lysis" of the melanocytes responsible for this skin hyperpigmentation is obtained for temperatures below −4° C.

Furthermore, most of the publications relate to mechanisms leading to cell mortality of the melanocytes for subzero temperature ranges. This is the case of osmotic shocks in cryobiology processes with phases of freezing the cells in liquid nitrogen (−196° C.).

In a known manner, mechanical and/or osmotic shocks occur following the formation of ice crystals which cause rupture of the cell membranes. Thus, these impacts only appear within a subzero temperature range.

In addition, many scientific publications underline that lowering the temperature within an above-zero temperature range (even up to 0° C.) does not affect cell viability (*General Guide for Cryogenically Storing Animal Cell Cultures*, Corning).

Although other studies indicate that a slight decrease in cell viability can be observed at above-zero temperatures, they specify however that this result can be obtained only over the long term (several days). However, these conditions are not compatible with the goal sought by the invention which aims to achieve this objective quasi-instantaneously, by means of a cosmetic treatment requiring only exposure of the cells at an above-zero temperature to the cryogenic fluid for a very short period (a few seconds) during the implementation of a sequence.

At around 20-25° C., most cells can survive, and even grow and metabolize for at least 3 or 4 days, or even more. However, there are cells which end up dying during exposure to moderate cold (but after several days) when the exposure time is sufficiently prolonged, whereas others remain living, and can multiply again if they are re-incubated at eugenic temperature. Indeed, many cells survive in the zone of +4° C. to +5° C., for periods that can range from 24 to 48 h. They are then subjected to no other apparent damage than an elongation of the latency time, when they are relocated at optimum temperature: they are slower to resume their multiplication.

It is effectively possible to retain very varied cell types at +4° C. for 6 to 9 weeks, provided that certain methodological rules are followed: (a) The cells must be in good condition at the time of cooling; (b) they must adhere to a substrate; (c) they must be cultivated in their usual culture medium; (d) the culture medium should not be changed during the storage period at 4° C.; (e) the culture medium must not be changed during the few days that follow the return to eugenic temperature. All these conditions were observed in our experiments.

In light of the prior art, there is therefore no reason to think that a significant mortality of the melanocytes could be observed whereas they have been held only at above-zero temperatures and far from the thermal threshold of their viability, for short periods.

Therefore, experiments (cell cultures-in vitro) were conducted in the context of the invention to determine the effects of different temperatures (+10, +5, 0, −5, −10, −15 and 16° C.) on the mortality of the melanocytes. Sequences were developed from the test bench (referenced, for example, EC-5 to reach a target temperature of −5° C.). A control group of cells was tested at +23° C. After 24 h of treatment, the cell mortality was quantified by assaying the expression of the proteins (see FIG. 1).

The results of these experiments showed that the variation in the mortality rate of the melanocytes as a function of the temperature was not always linear over the entire range of temperatures studied, contrary to what could be expected.

More precisely, the curve of the mortality rate as a function of temperature, which is represented by the graph of FIG. 1, is in three parts. A first part is linear and increasing and comprises the sequences EC16 (at −16° C.), EC−15 (at −15° C.) and EC−10 (at −10° C.), a second part is linear but in the form of a plateau and comprises the sequences EC−05 (−5° C.), ECO (at 0° C.), EC+05 (at +5° C.) and EC+10 (at +10° C.) then a third part is again linear and increasing and comprises the sequences ranging from EC+10 to EC+20 (at +20° C.).

It was observed that the mortality rate for the EC+10 sequence was very different from that obtained for the control group. These results show that different phenomena take place, even at positive epidermal temperatures, for extremely short sequences of time (less than 30 seconds).

In addition, the modification of cell viability occurs for very low temperature gradients, for example from +15° C. to +10° C. (i.e., a gradient of 8° C. in the case of experiment on cell cultures, where experimental conditions place the cells at a temperature of about 23° C. during the experiment).

Additional experiments were conducted in a higher temperature range (+20° C. to −15° C.) in order to confirm these results.

These data were completed by a study showing the effect of the temperature on the mortality of the melanocytes for sequences whose target temperatures reached were closer to each other so as to more precisely observe the influence of the dose of cryogenic fluid applied.

These observations made it possible to design cryogenic gas atomization sequences that make it possible to suddenly reduce the temperature of the epidermis while keeping it at above-zero temperatures, with the objective of limiting any inflammatory processes, irritations and transient hyperpigmentation (hyperpigmentation consecutive to the inflammatory process) encountered as much as possible, in particular, with the EC16 sequence (sequence inducing subzero temperature).

In addition, it was observed that lowering the cell temperature according to a gradient of 10° C. within an above-zero temperature range, beyond the ranges heretofore tested (for example, from +37 to +23° C.), did not result in the destruction of the cells. Indeed, it was observed that taking the incubation temperature of the melanocytes and of the keratinocytes (+37° C.) to a lower temperature (+23° C.) did not modify the viability of the cells. These data are therefore in opposition with the results of the study carried out over a range of +20 to +10° C.

The rate of change of the temperature of the epidermis does not inter-operate since the experiments showing variations in the temperature, respectively, of +37° C. to +23° C. and of +23° C. at +10° C. were carried out with high rates of change in both the temperature gradients. In cryogenics, three temperature descent mechanisms are generally distinguished. A slow descent corresponds substantially to a lowering of 5° C./min while a rapid descent occurs at 25° C./min and a so-called ultra-rapid descent at 100° C./min.

The mode of application of the cosmetic composition of the invention comprises, as shown in FIG. 4, a sequence of successive atomizations of the cryogenic fluid intended to cause, in contact with the skin, an ultra-rapid descent of its temperature from a starting temperature denoted (T0) (generally 34° C.) to a target temperature denoted (T1), or a gradient (T0−T1). This temperature drop is carried out in a given period of time or duration (t) and therefore at a certain speed or mechanism (denoted C1).

Due to the pause time, albeit relatively short, between two successive atomizations, the temperature of the epidermis tends to rise naturally in this interval. Therefore, this descent in temperature is accompanied by a series of (n) oscillations (that is, periodic variations of temperature) within a temperature range of the epidermis located between (T2, T3, T4 . . . ) for a given total time (t1). All these temperatures are above-zero and these oscillations can have a uniform or irregular period.

A first example of a sequence making it possible to obtain a reduction of about 40% of the viability of the melanocytes consists of the following values of the parameters with a number (n) of oscillations (and therefore of atomizations) equal to 4:

T0: +23.3° C.
T1: +14.5° C.
T2: +15.2° C.
T3: +15.0° C.
T4: +14.3° C.
t1=15 sec

Furthermore, an additional study confirmed that the number (n) of temperature oscillations of the epidermis also contributed to increasing the mortality rate of the melanocytes, it is provided that the cosmetic treatment of the invention may therefore comprise a series of 1 to 7 oscillations. Thus, a given sequence of atomizations corresponds to a number of oscillations, the respective durations of which and the amplitudes can vary.

The cryogenic properties of the fluid used in the cosmetic composition of the invention as well as the functionalities of the device envisaged for preparing this composition in situ make it possible to perform, in the laboratory, a temperature descent from 23° C. (which is the temperature of the cell cultures when they are handled) to −15.8° C. in 0.6 seconds, i.e. a speed of 76° C. per second or 4560° C./min. This is therefore ultra-rapid cooling.

However, there was no reason to think that a descent in the temperature of the epidermis with, for example, a gradient of 5° C. to 10° C., but without reaching subzero temperatures, can generate a significant mortality of the melanocytes and a disappearance of the dark spots.

Consequently, the cosmetic treatment method of the invention consists of delivering a dose of cryogenic fluid, by means of the device described above, in order to obtain a sudden lowering of the temperature of the cells of the epidermis with a high gradient (for example, of 8° C.), while keeping these cells in an above-zero temperature range.

However, this method is not carried out by applying a single and high instantaneous dose of cryogenic fluid which would have the risk of lowering the temperature of the epidermis below 0° C., but rather via several doses and typically between 1 and 7 doses, depending on the formulation chosen, these doses being delivered and applied to the epidermis via a sequence of successive atomizations of very short duration. This sequence thus produces oscillations of the temperature of the epidermis while remaining within an above-zero temperature range which unexpectedly makes it possible to reduce the viability of the melanocytes and therefore to treat skin hyperpigmentation.

Other tests conducted within the scope of the development of the invention have shown that an experiment bias existed in the measurement of the viability of the keratinocytes by protein assay. Indeed, the results of these tests showed, for certain temperatures (especially at temperature of +05° C.), a reduction in the viability of the keratinocytes.

This reduction is inconsistent with the viability limit (−35° C.) of the keratinocytes which is described in the literature. These tests therefore sought to explain this result and two assumptions were placed following the application on the epidermis of the cryogenic fluid present in the cosmetic composition.

According to a first hypothesis, a separation of the monolayer keratinocytes and the appearance of viable cells in the culture medium, and therefore in the rinsing media, thus causing an experimental bias by a "mechanical" reduction of the number of viable melanocytes in the Petri dish, occurs.

According to a second hypothesis, putting the melanocytes into quiescence stops their protein production by inducing a bias relative to the control group, the viability being calculated from the protein concentration.

More extensive research, within the scope of the invention, has been undertaken in order to verify the presence or absence of viable keratinocytes in rinsing media. These research has made it possible to demonstrate that the presence of very small quantities of keratinocytes in the rinsing media and therefore led to discarding the first hypothesis. Furthermore, the results clearly show, by virtue of microscopic observations, the presence of a monolayer of keratinocytes with viable cells. However, the granular appearance of this monolayer suggests a quiescent form of the cells thus enhancing the second hypothesis.

These last surprising and very advantageous results obtained with the implementation of the invention make it possible to cause the quiescence of keratinocytes (and, where appropriate, other cells) and to consider other possible applications.

Thus, neither the importance of the temperature gradient, nor its proximity to the cell viability threshold (+37° C.), nor the fact of proceeding only within an above-zero temperature range of the epidermis, nor the speed of lowering of the temperature, nor the number of oscillations, nor the very short duration of exposure to the cryogenic fluid, could cause the person skilled in the art to conclude that such a cosmetic treatment would lead to a significant reduction in skin hyperpigmentation on the epidermis.

To summarize, the invention thus proposes a cosmetic composition whose doses (micro-volumes) are formulated in situ by means of a very short sequence of atomizations (of duration typically between 0.01 s and 1 s) comprising successive atomizations of a cryogenic fluid for immediate application to the epidermis.

Thus, by a series of ultra-rapid temperature drops each followed by a short rise of the temperature (each descent and rise curve forming an oscillation of the temperature), this composition makes it possible to periodically lower the temperature of the epidermis initially at 34° C. (and therefore that of the melanocytes) according to a temperature gradient greater than 15° C. while keeping the epidermis in an above-zero temperature range during these drops in temperature, in a controlled manner.

Of course, the duration of the atomizations, their number, their frequency and the pauses in between, depend on the nature of the cryogenic fluid used, the flow rate of the solenoid valve used and other critical parameters. In theory, the duration of the sequence that comprises atomizations alternating with pauses is between 0.01 s and 206 seconds (for 7 atomizations), but is preferably less than 3.9 s. It is clear that in all cases and due to temperature rises after each spraying, the durations of the sequences will be longer than the atomization times. According to the invention, provision is made for the duration of the series of oscillations for each selected sequence to be between 2.1 s and 250 s.

An appropriate device intended for in situ preparation of the cosmetic composition of the invention comprises a pressurized cryogenic gas cartridge having specific physical properties, a spray nozzle ensuring the delivery of a precise dose of cryogenic gas from the cartridge by being coupled to automated timing means and a nozzle intended to concentrate, diffuse and apply the gas flow in a precise and homogeneous manner over a determined skin area.

One of the preferred embodiments of the treatment method of the invention making it possible to obtain the desired cosmetic result with respect to skin hyperpigmentation, comprises a sequence (referenced EC14) which consists of targeting, from a normal starting temperature of the epidermis of 34° C., a temperature of the epidermis of +14° C. obtained with 4 consecutive atomizations of cryogenic fluid.

This sequence thus comprises a series of 4 oscillations of the epidermal temperature. In this sequence, the opening durations of the solenoid valve (EV) integrated into the cryogenic device used (which exactly correspond to the atomization durations) are those indicated in Table 1 below:

TABLE 1

| Duration (s) | Solenoid valve state | Atomization # |
|---|---|---|
| 0 | 0 | |
| 0.5 | 1 | 1 |
| 0.60 | 0 | |
| 2.6 | 1 | 2 |
| 2.66 | 0 | |
| 2.7 | 0 | |
| 2.9 | 0 | |
| 3.0 | 0 | |
| 3.7 | 0 | |
| 4.4 | 0 | |
| 4.5 | 0 | |
| 5.3 | 0 | |
| 6.0 | 1 | 3 |
| 6.06 | 0 | |
| 6.5 | 0 | |
| 9.0 | 1 | 4 |
| 9.06 | 0 | |
| 20.0 | 0 | |

In this table 1, the position of the solenoid valve referenced "0" corresponds to a sealed closed position of the solenoid valve that allows no gas to pass through, while the state "1" corresponds to an open position for expansion and ejection of the cryogenic gas. It therefore emerges from Table 1 that the atomization phases are here between 0.06 seconds (atomizations No. 2, 3 and 4) and 0.1 second (atomization No. 1), the duration of the oscillations then being between 2 and 3 seconds.

The volumes of gas pulses each opening of the solenoid valve may be calculated on the basis of the opening durations given in Tables 1 (above) and 2 (below) by taking as reference an average of the dev of the cryogenic gas at the outlet of the solenoid valve.

The dosage, or in other words, the doses of cryogenic fluid applied to the epidermis and making it possible to obtain the desired cosmetic effect thus ranges (in combination with successive volumes of fluid atomized during a sequence) from 0.08 mL with 1,1-difluoroethane gas (for the sequence EC14 with a single atomization and therefore a single oscillation) to 3.50 mL (for sequence EC00 with the same gas and 7 oscillations). This result is obtained by always beginning from a starting temperature of the epidermis of +34° C., reaching the target temperature (0° C.), then rising to a temperature of at least +20° C. and doing so 7 times in total and using an average solenoid valve output flow of 0.8 mL/second. More generally, these doses are a function of the nature of the cryogenic fluid used (and therefore its boiling point) as well as of the escape flow of the solenoid valve (and therefore of its structural characteristics) and of its opening duration.

The low (i.e., target) but still above-zero temperatures of the epidermis obtained following the atomizations referenced 1 to 4 (averaged across 5 tests) are, respectively, 12.1° C., 13.6° C., 13.6° C. then 13.0° C., the temperature rising at each oscillation above 20° C. (see FIGS. 4 and 5).

Other examples of implementation of the cosmetic treatment method of the invention are detailed below in Table 2 with various atomization sequences. In these sequences referenced (EC), the opening periods (in seconds) of the solenoid valve (EV) integrated into the cryogenic device used with the 1,1-difluoroethane gas are associated with a flow rate of the solenoid valve of 0.8 mL/second.

In the following table 2, each sequence (EC) is associated with a code indicating the target temperature and the number of oscillations. The sequences start with the solenoid valve (EV) in the closed position. The term (Pu) corresponds to the duration of an opening of the solenoid valve and therefore to atomizing for a given time and at a flow rate set at 0.8 mL/s. The term (Pa) corresponds to the closing time of the solenoid valve between two atomizations. This time corresponds to a pause (Pa) resulting in a natural rise in the temperature of the epidermis above 20° C. The sequence EC14/4 is shown in FIGS. 3 and 5.

The development of the invention has given rise to numerous experiments relating to the optimization of atomization sequences. These sequences were tested on cell culture models in order to determine, in particular, their incidence on the cell viability of the melanocytes and keratinocytes. The main markers of irritation were also measured.

The first objective of these experiments was to select cyto-selective sequences, that is, those which act only on the melanocytes by reducing their viability while preserving keratinocytes (concept of performance).

A second objective was to determine the sequences which generated as low a variation in the irritation markers as possible (concept of risk). In summary, the sequences whose performance/risk ratio was optimal were selected.

Among the sequences tested during these experiments, 4 sequences had an optimal performance/risk ratio. These are sequences referenced EC+14/1 osc, EC+14/4 osc, EC+12/2 osc and EC00/7 osc which are explicitly mentioned in Table 2. These sequences were carried out with a solenoid valve whose exhaust flow rate is 0.8 mL/s. Each dose of cryogenic gas thus corresponds to the product of the duration of the atomization multiplied by this flow rate.

Among the other sequences tested, variants (for example, the sequence EC+14/3 osc) were close to this optimal ratio and must be considered as falling within the scope of the invention. Generally, all the sequences between EC+14/1 osc and EC00/7 osc, both from the point of view of above-zero target temperatures and the number of oscillations, are of interest for the formulation of the cosmetic composition of the invention. Other studies that were conducted on epidermises treated with the cosmetic composition of the invention confirm these results.

TABLE 2

| Seq. | Total dose (mL) | Atomizations (Pu)/Pa (Pauses) in seconds Pu/Pa 1 | Pu/Pa 2 | Pu/Pa 3 | Pu/Pa 4 | Pu/Pa 5 | Pu/Pa 6 | Pu/Pa 7 |
|---|---|---|---|---|---|---|---|---|
| EC14/1 | 0.080 | 0.1 | | | | | | |
| EC14/4 | 0.296 | 0.18/0.58 | 0.07/0.67 | 0.06/0.84 | 0.06 | | | |
| EC12/2 | 0.240 | 0.22/0.68 | 0.08 | | | | | |
| EC00/7 | 3.432 | 0.5/18.8 | 0.5/24.7 | 0.5/34.2 | 0.5/35.3 | 0.6/44.4 | 0.6/44.1 | 0.7 |

The invention claimed is:

1. A method for cosmetic treatment of skin hyperpigmentation by means of a pressurized cartridge containing a cryogenic fluid, wherein the boiling point of the cryogenic fluid is between −196° C. and −19° C. and a device comprising a solenoid valve controlled by an electronic timing system and ensuring expansion of the fluid from said cartridge and a spray nozzle ensuring its ejection and atomization onto an epidermis, wherein a sequence of successive atomizations of said fluid is carried out on the epidermis whose durations are between 0.01s and Is to create, within a target temperature range between 0° C. and 14° C., a series of 1 to 7 oscillations of its temperature, a total duration of which is between 2.1 seconds and 250 seconds, said sequence comprising, between each atomization, an abrupt cooling phase at a temperature descent rate comprised between 50° C./s and 170° C./s followed by a slower warming phase between 20° C. and 34° C.

2. The method according to claim 1, wherein the duration of each of the oscillations is between 0.2 seconds and 3 seconds.

3. The method according to claim 1, wherein the phase of cooling the epidermis is carried out according to a gradient of at least 15° C. from an initial temperature of between 29° C. and 37° C.

4. The method according to claim 1, wherein it comprises an in situ formulation of a cryogenic gas said cryogenic gas is selected from the group consisting of 1,1-difluoroethane, the boiling point of which is −24.7° C. under normal pressure of 1 atmosphere), methoxymethane, 1,1,1,2-tetrafluoroethane, trans-1,3,3,3-tetrafluoropropene, butane/propane mixtures respectively having boiling temperatures of −196° C., −24° C., −26.3° C. and −19° C., each under normal pressure of 1 atmosphere.

5. The method according to claim 1, wherein said sequence is implemented by means of a single atomization of 1,1-difluoroethane at 0.8 mL/second for a duration of 0.1 second so as to achieve a target epidermis temperature of 14° C.

6. The method according to claim 1, wherein said sequence is implemented by means of 4 successive atomizations of 1,1-difluoroethane at 0.8 mL/second, each having a duration comprised between 0.06 seconds and 0.18 seconds so as to achieve a target epidermis temperature of 14° C. after each atomization.

7. The method according to claim 1, wherein said sequence is implemented by means of 2 successive atomizations of 1,1-difluoroethane at 0.8 mL/second, each having a duration comprised of 0.22 seconds and 0.08 seconds respectively so as to achieve a target epidermis temperature of 12° C. after each atomization.

8. The method according to claim 1, wherein said sequence is implemented by means of 7 successive atomizations of 1,1-difluoroethane at 0.8 mL/second, each having a duration comprised between 0.5 seconds and 0.7 seconds so as to achieve a target epidermis temperature of 0° C. after each atomization.

* * * * *